United States Patent
Holmes

(10) Patent No.: US 9,314,096 B1
(45) Date of Patent: Apr. 19, 2016

(54) RECHARGEABLE TOOTHPASTE-DISPENSING TOOTHBRUSH ASSEMBLY

(71) Applicant: Michelle L. Holmes, Rahway, NJ (US)

(72) Inventor: Michelle L. Holmes, Rahway, NJ (US)

( * ) Notice: Subject to any disclaimer, the term of this patent is extended or adjusted under 35 U.S.C. 154(b) by 456 days.

(21) Appl. No.: 13/856,042

(22) Filed: Apr. 3, 2013

(51) Int. Cl.
*A46B 13/04* (2006.01)

(52) U.S. Cl.
CPC ...................................... *A46B 13/04* (2013.01)

(58) Field of Classification Search
CPC .... A46B 13/04; A46B 15/0044; A46B 17/04; A46B 11/002; A46B 11/0065; A46B 11/0096; A46B 11/0041; A46B 2200/1066
USPC .................. 401/163, 164, 152, 171
See application file for complete search history.

(56) References Cited

U.S. PATENT DOCUMENTS

| | | | |
|---|---|---|---|
| 4,332,497 A | 6/1982 | Rodriguez | |
| 4,583,563 A | 4/1986 | Turner | |
| 5,048,144 A * | 9/1991 | Andrews | 15/184 |
| 5,062,728 A * | 11/1991 | Kuo | 401/176 |
| D349,605 S | 8/1994 | Schneider et al. | |
| 5,927,889 A * | 7/1999 | La Flower | 401/268 |
| D419,775 S | 2/2000 | Sidhu | |
| 6,206,600 B1 | 3/2001 | Rosenberg et al. | |
| 6,257,791 B1 | 7/2001 | Scamard | |
| 6,273,629 B1 | 8/2001 | Jordan | |
| 6,798,169 B2 | 9/2004 | Stratmann et al. | |
| 7,617,828 B1 | 11/2009 | Sinha | |
| 2009/0273244 A1* | 11/2009 | Luo | 310/38 |
| 2010/0272500 A1* | 10/2010 | Martin et al. | 401/277 |
| 2010/0327803 A1* | 12/2010 | Katsura | 320/108 |
| 2012/0103355 A1* | 5/2012 | Bowie | 132/200 |

* cited by examiner

*Primary Examiner* — David Walczak
*Assistant Examiner* — Bradley Oliver

(57) ABSTRACT

A rechargeable toothpaste-dispensing toothbrush assembly stores and dispenses toothpaste while also providing a charger to recharge the assembly. The assembly includes an elongated member having a handle. A surface is removably coupled to the elongated member. A plurality of bristles is coupled to the surface. A toothpaste cartridge is positionable in the handle. A plunger is coupled to the handle and positioned adjacent to the toothpaste cartridge. The plunger is operationally engaged to the toothpaste cartridge. A button is coupled to the handle and is operationally coupled to the plunger wherein the plunger engages the toothpaste cartridge upon manipulation of the button wherein the button is configured for dispensing toothpaste from the toothpaste cartridge to the bristles.

16 Claims, 6 Drawing Sheets

RECHARGEABLE TOOTHPASTE-DISPENSING TOOTHBRUSH ASSEMBLY

BACKGROUND OF THE DISCLOSURE

Field of the Disclosure

The disclosure relates to toothbrush assemblies and more particularly pertains to a new toothbrush assembly for storing and dispensing toothpaste while also providing a charger to recharge the assembly.

SUMMARY OF THE DISCLOSURE

An embodiment of the disclosure meets the needs presented above by generally comprising an elongated member having a handle. A surface is removably coupled to the elongated member. A plurality of bristles is coupled to the surface. A toothpaste cartridge is positionable in the handle. A plunger is coupled to the handle and positioned adjacent to the toothpaste cartridge. The plunger is operationally engaged to the toothpaste cartridge. A button is coupled to the handle and is operationally coupled to the plunger wherein the plunger engages the toothpaste cartridge upon manipulation of the button wherein the button is configured for dispensing toothpaste from the toothpaste cartridge to the bristles.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
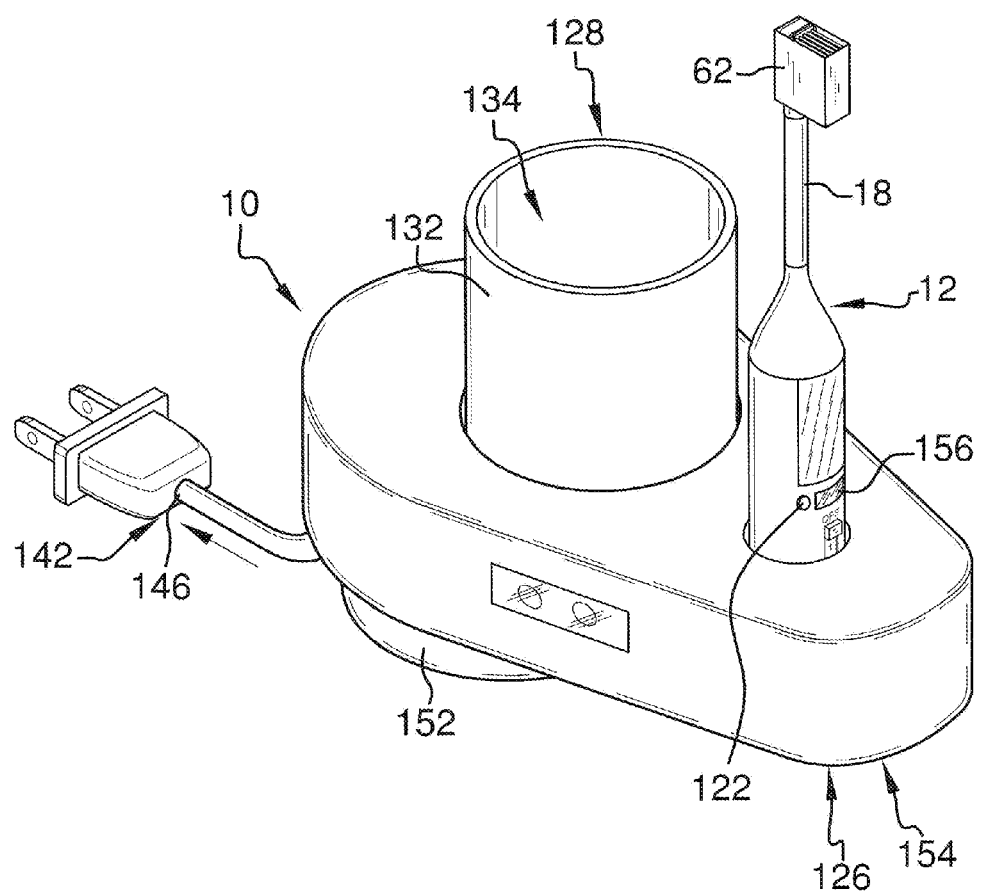
FIG. 1 is a top front side perspective view of a rechargeable toothpaste-dispensing toothbrush assembly according to an embodiment of the disclosure.
Figure 2:
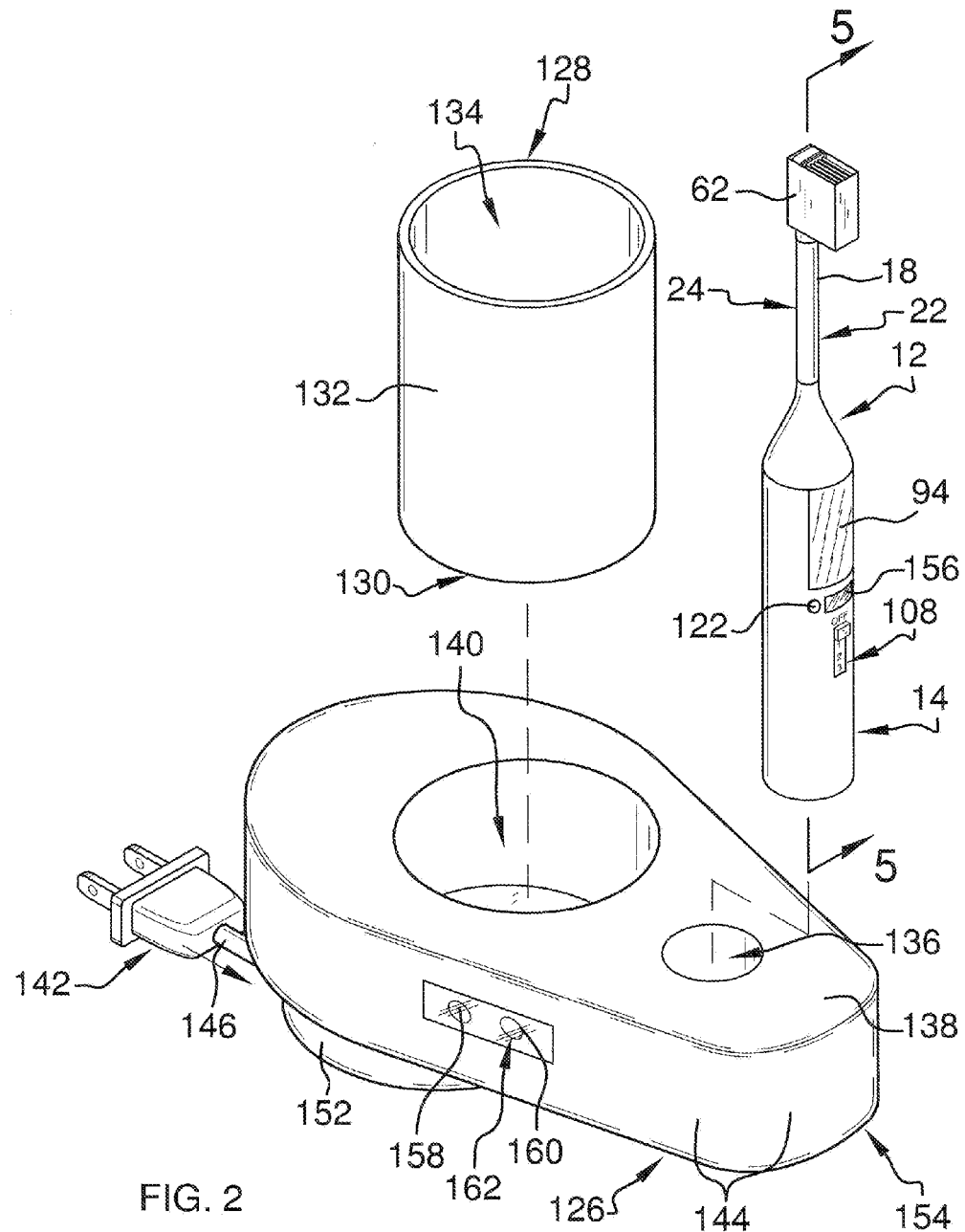
FIG. 2 is a partially-exploded top front side perspective view of an embodiment of the disclosure.
Figure 3:
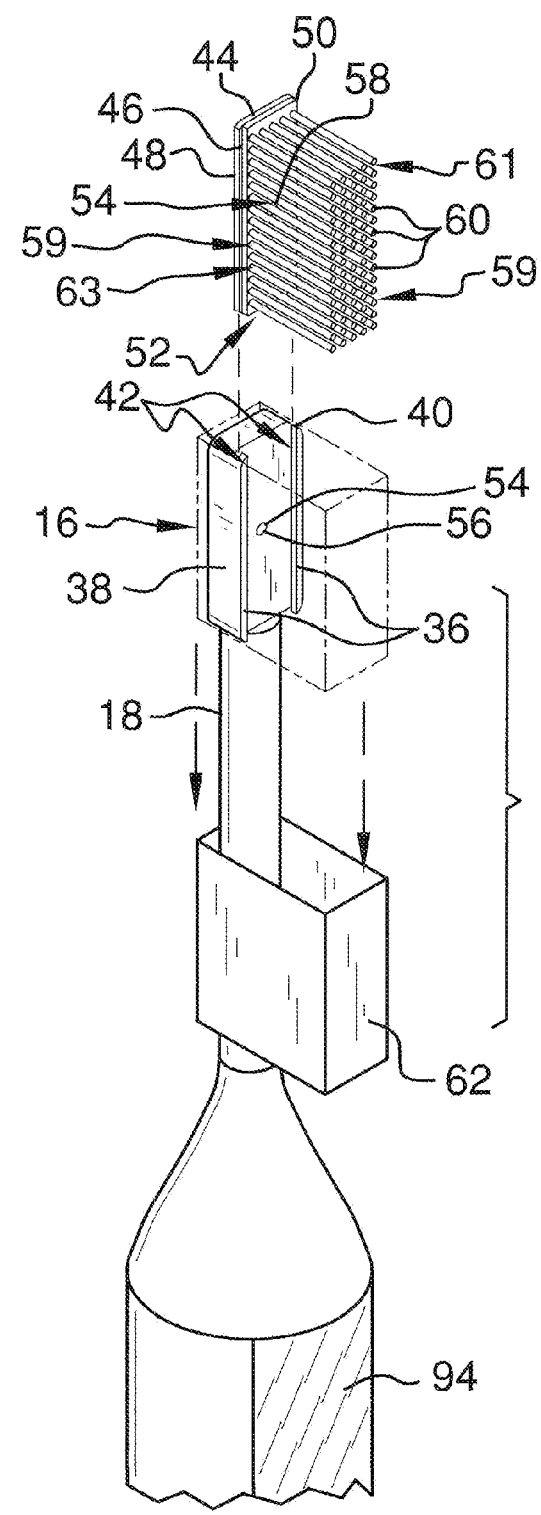
FIG. 3 is a top front side perspective view of an elongated member and a cover of an embodiment of the disclosure.
Figure 4:
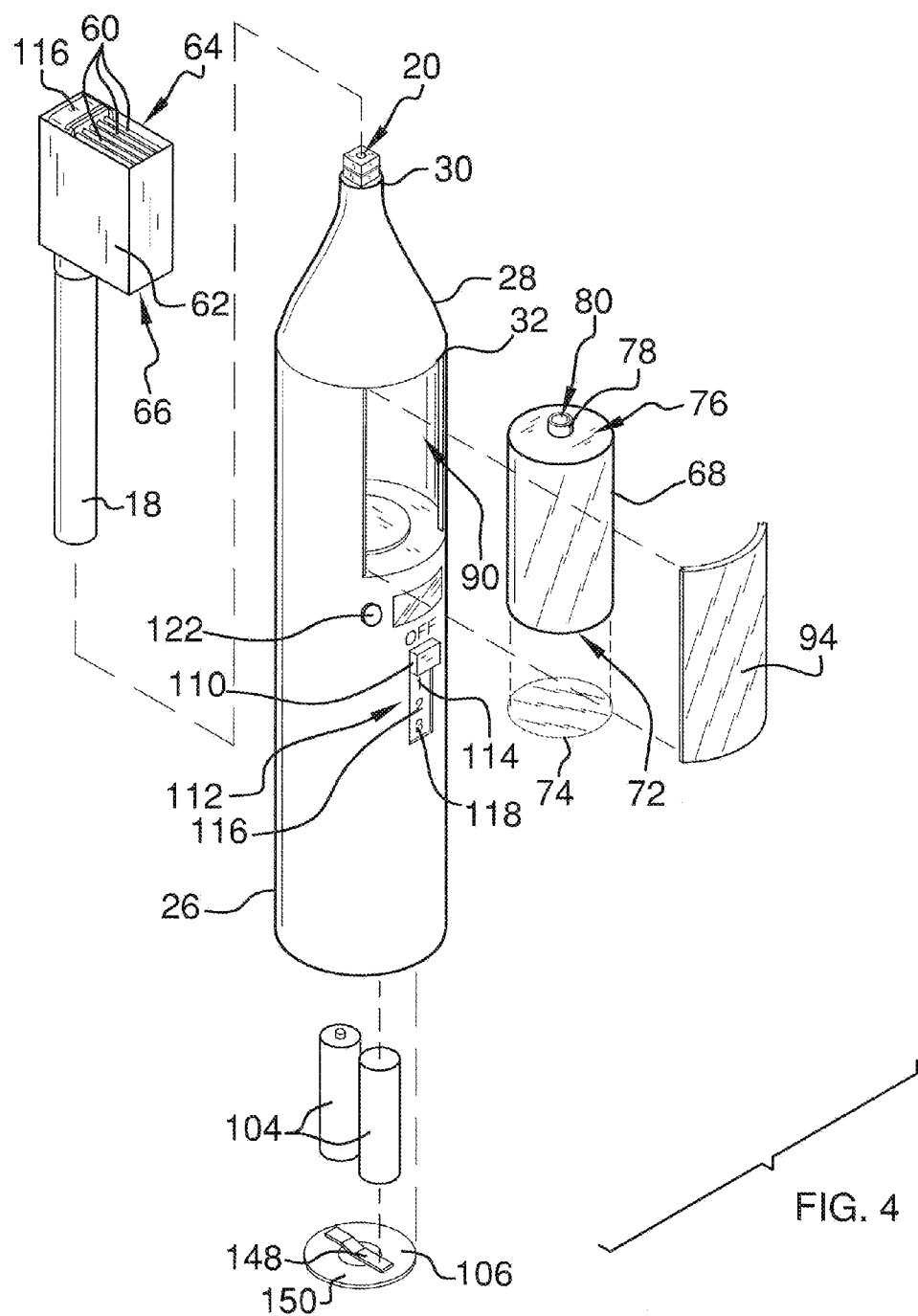
FIG. 4 is a partially-exploded top front side perspective view of an elongated member and a cover of an embodiment of the disclosure.
Figure 5:
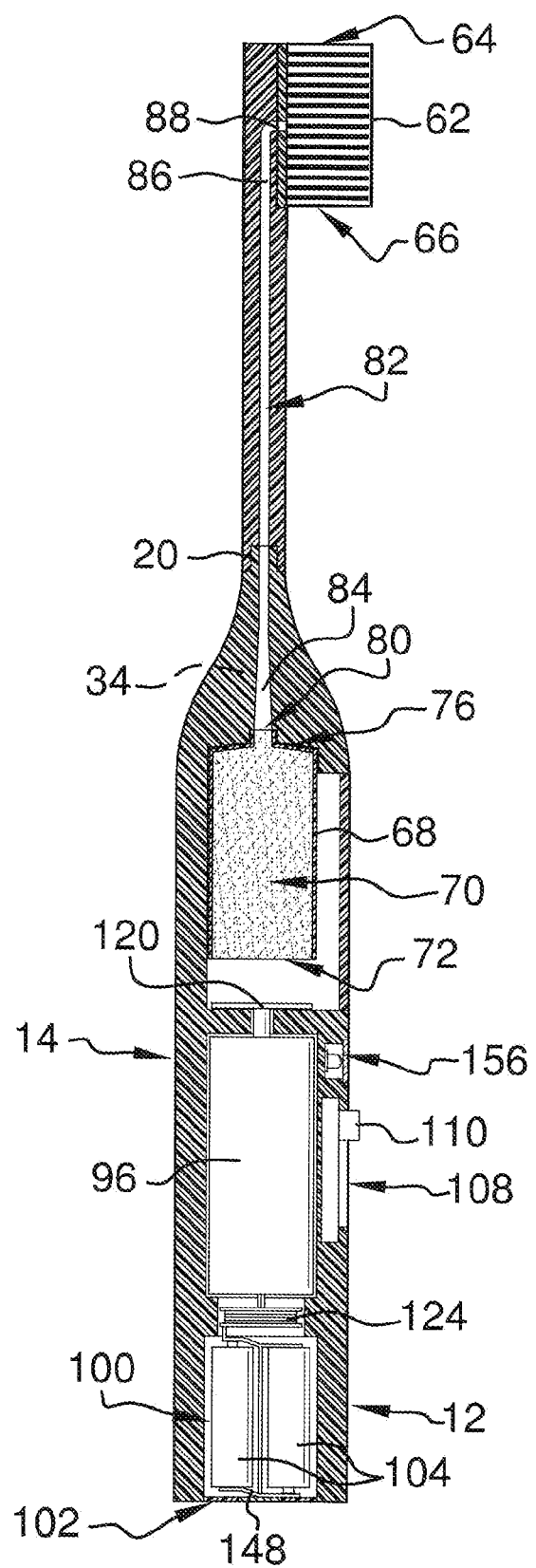
FIG. 5 is a cross-sectional side view of an embodiment of the disclosure in the off position taken along line 5-5 of FIG. 2.
Figure 6:
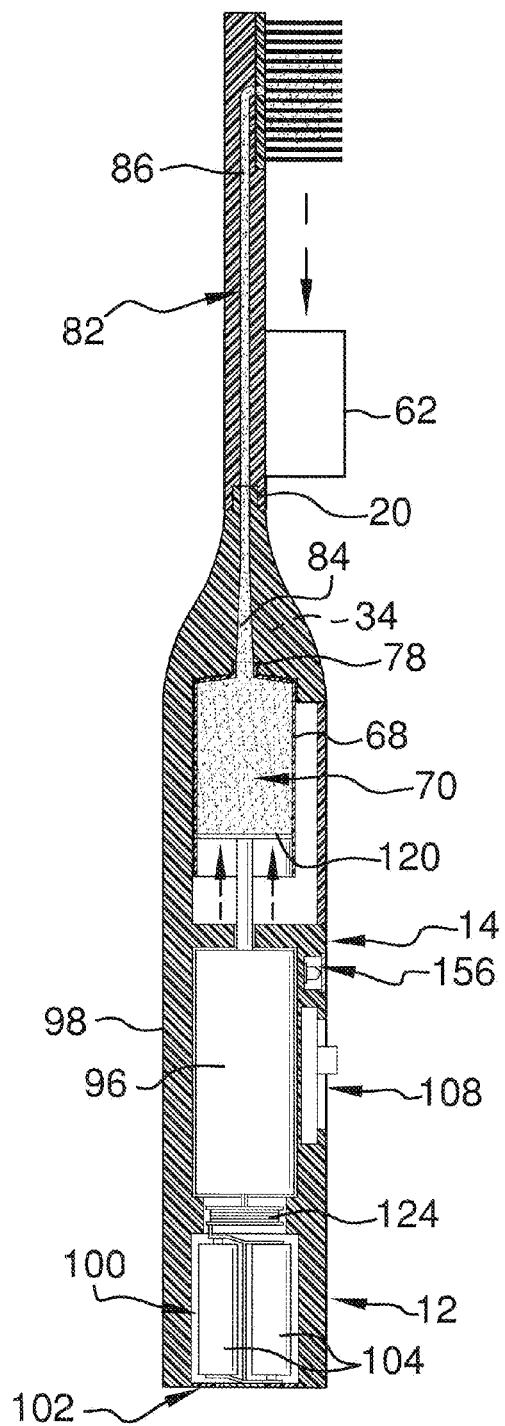
FIG. 6 is a cross-sectional side view similar to FIG. 5 except that FIG. 6 shows an embodiment of the disclosure with the cover slid off of the head and the motor running.

With reference now to the drawings, and in particular to FIGS. 1 through 6 thereof, a new toothbrush assembly embodying the principles and concepts of an embodiment of the disclosure and generally designated by the reference numeral 10 will be described.

As best illustrated in FIGS. 1 through 6, the rechargeable toothpaste-dispensing toothbrush assembly 10 generally comprises an elongated member 12 having a handle 14, a head 16, and a neck 18. The neck 18 is positioned between the head 16 and the handle 14 and may be slightly angled relative to the head 16. A coupler 20 removably couples the neck 18 and the handle 14 wherein the neck 18 may be removed for cleaning. The head 16 is transversely positioned relative to the handle 14. The elongated member 12 has a top side 22 positioned opposite a bottom side 24. The top side 22 of the handle 14 has a lower portion 26 and an upper portion 28 wherein the upper portion 28 has a top peripheral edge 30 and the lower portion 26 has a bottom peripheral edge 32. The bottom peripheral edge 32 has a larger circumference than the top peripheral edge 30 wherein the top side 22 of the handle 14 is substantially cone-shaped such that the handle 14 extends inwardly from the bottom peripheral edge 32 toward the top peripheral edge 30. An interior space 34 extends through the elongated member 12. The elongated member 12 is preferably made from a thick, durable plastic so as to protect the interior space 34 from damage and moisture.

A pair of tabs 36 is coupled to the head 16. The tabs 36 extend from opposite ends 38, 40 of the top side 22 of the head 16. A pair of slots 42 is formed between the tabs 36 and the head 16. A surface 44 is removably coupled to the head 16 wherein the surface 44 is interchangeable with another one of the surfaces 44. The surface 44 has a pair of projections 46 extending outwardly from opposite ends 48, 50 of a top side 52 of the surface 44. The projections 46 have a size and shape corresponding to the slots 42 wherein the projections 46 are couplable to the slots 42 when the projections 46 are slidably inserted into the slots 42. A pair of holes 54 is provided. A first one 56 of the holes 54 is positioned in the head 16 and a second one 58 of the holes 54 is positioned in the surface 44. The first one 56 of the holes 54 is centrally positioned in the top side 22 of the head 16 and the second one 58 of the holes 54 is positioned centrally in the top side 52 of the surface 44. A plurality of bristles 60 is coupled to and extends outwardly from the surface 44. The bristles 60 extend from the top side 52 of the surface 44 between each of the projections 46. A plaque remover 59 is coupled to the bristles 60. The plaque remover 59 is coupled to a top end 61 and a bottom end 63 of the bristles 60. A flexible cover 62 is coupled to the head 16. The cover 62 has an open top end 64 and an open bottom end 66 wherein the cover 62 is selectively positionable over the bristles 60 when the head 16 is positioned between the open top and bottom ends 64, 66 and is selectively positionable on the neck 18 below the bristles 60 when the cover 62 is pushed downward away from the bristles 60. The cover 62 is preferably made from plastic material.

A toothpaste cartridge 68 is positionable in the interior space 34 of the handle 14. The toothpaste cartridge 68 is cylindrical and configured to store and dispense toothpaste 70. A bottom side 72 of the toothpaste cartridge 68 has a thin covering 74. A top side 76 of the toothpaste cartridge 68 has an outwardly projecting ring 78 wherein the ring 78 has an aperture 80 positioned centrally therein. A conduit 82 is positioned in the elongated member 12. The conduit 82 has a first end 84 in fluid communication with the toothpaste cartridge 68 and a second end 86 positioned proximate the bristles 60 wherein the conduit 82 is configured for delivering toothpaste 70 from the toothpaste cartridge 68 to the bristles 60. The first end 84 of the conduit 82 is coupled to the ring 78 of the toothpaste cartridge 68 and the second end 86 of the conduit 82 is coupled to the hole 54 in the head 16. The second end 86 of the conduit 82 comprises a curved portion 88 wherein the curved portion 88 is positioned parallel to the bristles 60 when the surface 44 is coupled to the head 16. The conduit is preferably made from plastic material. An opening 90 extends through the handle 14 into the interior space 34 wherein the opening 90 is configured for selectively inserting and removing the toothpaste cartridge 68 from the interior space 34. The opening 90 extends through a top side 22 of the handle 14. A door 94 is coupled to the handle 14 and is selectively positionable such that the door 94 closes the opening 90. The door 94 is transparent wherein the door 94 is configured for viewing a level of toothpaste 70 held in the interior space 34 such that a user is alerted to low levels of toothpaste 70 and can insert a new toothpaste cartridge 68 when necessary.

A motor 96 is coupled to the handle 14 and extends across the interior space 34. The motor 96 is positioned in a medial section 98 of the handle 14. A battery compartment 100 is coupled to the handle 14 and is positioned in the interior space 34 in a bottom end 102 of the handle 14. The battery compartment 100 is configured for holding a pair of batteries 104. The battery compartment 100 is electrically coupled to the motor 96 wherein the battery compartment 100 activates the motor 96 and thereby moves the head 16 when the batteries 104 deliver power to the motor 96. An end cap 106 is couplable to the handle 14. The end cap 106 is selectively couplable to the bottom end 102 of the handle 14 wherein the end cap 106 is configured to store the batteries 104 inside the battery compartment 100. A control 108 is coupled to the handle 14 and is positioned on the top side 22 of the handle 14 below the opening 90. The control 108 is operationally coupled to the motor 96 and the battery compartment 100 wherein selectively manipulating the control 108 activates the motor 96. The control 108 further comprises an off position 110 and a plurality of speed settings 112. The speed settings 112 comprise a low speed setting 114, a medium speed setting 116, and a high speed setting 118 wherein the low speed setting 114 is slower than the medium speed setting 116 and the medium speed setting 116 is slower than the high speed setting 118.

A plunger 120 is coupled to the handle 14 and extends across the interior space 34. The plunger 120 couples the toothpaste cartridge 68 and the motor 96 and is operationally engaged to the toothpaste cartridge 68. A button 122 is coupled to the handle 14. The button 122 is operationally coupled to the plunger 120 wherein the plunger 120 engages the toothpaste cartridge 68 upon manipulation of the button 122 wherein the button 122 is configured for dispensing toothpaste 70 from the toothpaste cartridge 68 to the bristles 60. Manipulating the button 122 dispenses a predetermined amount of toothpaste 70 that is suitable for one use. A coil 124 is coupled to the handle 14 and extends across the interior space 34. The coil 124 is positioned between the battery compartment 100 and the motor 96 and is electrically coupled to both the battery compartment 100 and the motor 96.

A hub 126 is provided. The hub 126 is substantially oval-shaped. A cup 128 is couplable to the hub 126. The cup 128 has a bottom end 130 and a peripheral wall 132 extending upwardly from the bottom end 130 wherein the bottom end 130 and the peripheral wall 132 define an interior space 134 for holding a fluid. The interior space 134 of the cup 128 is dimensioned to receive between approximately 80 grams and 140 grams. The cup 128 may be made from a dishwasher-safe material. A toothbrush cavity 136 is coupled to the hub 126 and extends downwardly into a top side 138 of the hub 126. The toothbrush cavity 136 has a size and shape corresponding to the bottom side 102 of the handle 14 wherein the toothbrush cavity 136 is configured to receive the elongated member 12 when the bottom side 102 of the handle 14 is positioned in the toothbrush cavity 136. A cup cavity 140 is coupled to the hub 126 and extends downwardly into the top side 138 of the hub 126. The cup cavity 140 has a size and shape corresponding to the bottom end 130 of the cup 128 wherein the cup cavity 140 is configured to receive the cup 128 when the bottom end 130 of the cup 128 is positioned in the cup cavity 140.

A power cord 142 is coupled to the hub 126 and extends outwardly from one of a plurality of sides 144 of the hub 126. A first end 146 of the power cord 142 is retractable into the hub 126. The first end 146 of the power cord 142 may also be wrapped around the hub 126. The power cord 142 is operationally coupled to the hub 126 wherein the power cord 142 is configured to deliver power to the hub 126 when the first end 146 of the power cord 142 is coupled to an electrical outlet. A contact 148 is coupled to the end cap 106 and extends across an inner surface 150 of the end cap 106. The contact 148 forms a closed circuit when the handle 14 is positioned in the toothbrush cavity 136 and is receiving electrical power from the hub 126. A suction cup 152 is coupled to the hub 126 and extends downwardly from a bottom side 154 of the hub 126 wherein the suction cup 152 is configured to secure the suction cup 152 to an exterior surface when the suction cup 152 is pressed downwardly against the exterior surface.

A first indicator 156 is coupled to the handle 14 and is positioned below the opening 90 and above the control 108. The first indicator 156 is operationally coupled to the battery compartment 100 wherein the first indicator 156 emits a charged light 158 when the batteries 104 in the battery compartment 100 have a full charge and emits an uncharged light 160 when the batteries 104 are low on charge. A second indicator 162 is coupled to the hub 126 and is positioned on one of the sides 144 of the hub 126. The second indicator 162 is operationally coupled to the battery compartment 100 wherein the second indicator 162 emits a charged light 158 when the batteries 104 in the battery compartment 100 have a full charge and emits an uncharged light 160 when the batteries 104 are low on charge. The first and second indicators 156, 162 are both small, fluorescent lights. The assembly 10 may be stored in a mesh bag. The mesh bag may have indicia positioned thereon, such as a logo, and may also have a strap. The assembly 10 has a height between approximately 10 centimeters and 40 centimeters and a width between approximately 5 centimeters and 25 centimeters.

In use, as stated above and shown in the Figures, the cover 62 is slid off of the head 16. The toothpaste cartridge 68 is inserted into the opening 90. The door 94 is positioned to close the opening 90. The button 122 and the control 156 are manipulated and the bristles 60 are positioned against a user's teeth. After use, the control 156 is manipulated to deactivate the motor 96. A user rinses with the cup 128 and then rinses the bristles 60. The cover 62 is slid back onto the head 16 over the bristles 60. The elongated member 12 is placed into the toothbrush cavity 136 to charge.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A rechargeable toothpaste-dispensing toothbrush assembly comprising:
   an elongated member having a handle;
   an interior space extending through said elongated member;
   a surface removably coupled to said elongated member;
   a plurality of bristles coupled to said surface;
   a toothpaste cartridge positionable in said handle, said toothpaste cartridge being positionable in said interior space;
   a plunger coupled to said handle and positioned adjacent to said toothpaste cartridge, said plunger being operationally engaged to said toothpaste cartridge;
   a button coupled to said handle, said button being operationally coupled to said plunger wherein said plunger engages said toothpaste cartridge upon manipulation of said button wherein said button is configured for dispensing toothpaste from said toothpaste cartridge to said bristles;
   an opening extending through said handle into said interior space wherein said opening is configured for selectively inserting and removing said toothpaste cartridge from said interior space;
   a door coupled to said handle, said door being selectively positionable such that said door closes said opening;
   a motor coupled to said handle and extending across said interior space;
   a battery compartment coupled to said handle and being positioned in said interior space, said battery compartment being configured for holding a pair of batteries, said battery compartment being electrically coupled to said motor wherein said battery compartment activates said motor;
   a control coupled to said handle, said control being operationally coupled to said motor and said battery compartment wherein selectively manipulating said control activates said motor;
   a hub, said hub being substantially oval-shaped;
   a toothbrush cavity coupled to said hub, said toothbrush cavity extending downwardly into a top side of said hub, said toothbrush cavity having a size and shape corresponding to said bottom side of said handle wherein said toothbrush cavity is configured to receive said elongated member when said bottom side of said handle is positioned in said toothbrush cavity;
   a power cord coupled to said hub, said power cord being operationally coupled to said hub wherein said power cord is configured to deliver power to said hub when a first end of said power cord is coupled to an electrical outlet;
   a cup couplable to said hub, said cup having a bottom end; and
   a cup cavity coupled to said hub, said cup cavity extending downwardly into said top side of said hub, said cup cavity having a size and shape corresponding to said bottom end of said cup wherein said cup cavity is configured to receive said cup when said bottom end of said cup is positioned in said cup cavity.

2. The assembly of claim 1, further comprising:
   a head and a neck of said elongated member, said neck being positioned between said head and said handle;
   a pair of tabs coupled to said head, said tabs extending from opposite ends of a top side of said head;
   a pair of slots being formed between said tabs and said head; and
   a pair of projections of said surface, said projections extending outwardly from opposite ends of a top side of said surface, said projections having a size and shape corresponding to said slots wherein said projections are couplable to said slots when said projections are slidably inserted into said slots.

3. The assembly of claim 2, further comprising a pair of holes, a first one of said holes being positioned in said head, a second one of said holes being positioned in said surface, said first one of said holes being positioned centrally in said top side of said head, said second one of said holes being positioned centrally in said top side of said surface.

4. The assembly of claim 2, further comprising a coupler removably coupling said neck and said handle.

5. The assembly of claim 1, further comprising:
   said plurality of bristles coupled to and extending outwardly from said surface, said bristles extending from a top side of said surface.

6. The assembly of claim 5, further comprising a flexible cover coupled to said elongated member, said cover having an open top end and an open bottom end wherein said cover is selectively positionable over said bristles when said head is positioned between said open top and bottom ends.

7. The assembly of claim 1, further comprising said door being transparent wherein said door is configured for viewing a level of toothpaste held in said interior space.

8. The assembly of claim 1, further comprising a conduit positioned in said elongated member, said conduit having a first end in fluid communication with said toothpaste cartridge and a second end positioned proximate said bristles wherein said conduit is configured for delivering toothpaste from said toothpaste cartridge to said bristles.

9. The assembly of claim 8, further comprising said first end of said conduit being coupled to a ring of said toothpaste cartridge and a second end of said conduit being coupled to a hole in said head.

10. The assembly of claim 1, further comprising:
    said plunger extending across said interior space, said plunger coupling said toothpaste cartridge and said motor, said plunger being operationally engaged to said toothpaste cartridge; and
    said button being operationally coupled to said plunger wherein said plunger engages said toothpaste cartridge upon manipulation of said button wherein said button is configured for dispensing toothpaste from said toothpaste cartridge to said bristles.

11. The assembly of claim 1, further comprising a suction cup coupled to said hub, said suction cup extending downwardly from a bottom side of said hub wherein said suction cup is configured to secure said suction cup to an exterior surface when said suction cup is pressed downwardly against the exterior surface.

12. The assembly of claim 1, further comprising:
    a first indicator coupled to said handle, said first indicator being operationally coupled to said battery compartment wherein said first indicator emits a charged light when the batteries in said battery compartment have a full charge and emits an uncharged light when the batteries are low on charge; and a second indicator coupled to said hub, said second indicator being operationally coupled to said battery compartment wherein said second indicator emits a charged light when the batteries in said battery compartment have a full charge and emits an uncharged light when the batteries are low on charge.

13. The assembly of claim 1, further comprising a contact, said contact forming a closed circuit when said handle is positioned in said toothbrush cavity and is receiving electrical power from said hub.

14. The assembly of claim 1, further comprising an end cap couplable to said handle, said end cap being selectively couplable to a bottom side of said handle wherein said end cap is configured to store the batteries inside said battery compartment.

15. The assembly of claim 1, further comprising a coil coupled to said handle and extending across said interior space, said coil being positioned between said battery compartment and said motor, said coil being electrically coupled to said battery compartment and said motor.

16. A rechargeable toothpaste-dispensing toothbrush assembly comprising:
- an elongated member having a handle, a head, and a neck, said neck being positioned between said head and said handle, said head being transversely positioned relative to said handle, said elongated member having a top side positioned opposite a bottom side, said top side of said handle having a lower portion and an upper portion, said upper portion having a top peripheral edge and said lower portion having a bottom peripheral edge, said bottom peripheral edge having a larger circumference than said top peripheral edge wherein said top side of said handle is substantially cone-shaped such that said handle extends inwardly from said bottom peripheral edge toward said top peripheral edge;
- an interior space extending through said elongated member;
- a pair of tabs being coupled to said head, said tabs extending from opposite ends of said top side of said head;
- a pair of slots being formed between said tabs and said head;
- a surface being removably coupled to said head wherein said surface is interchangeable with another one of said surfaces, said surface having a pair of projections, said projections extending outwardly from opposite ends of a top side of said surface, said projections having a size and shape corresponding to said slots wherein said projections are couplable to said slots when said projections are slidably inserted into said slots;
- a pair of holes, a first one of said holes being positioned in said head, a second one of said holes being positioned in said surface, said first one of said holes being positioned centrally in said top side of said head, said second one of said holes being positioned centrally in said top side of said surface;
- a plurality of bristles coupled to and extending outwardly from said surface, said bristles extending from said top side of said surface, said bristles extending between each of said projections;
- a flexible cover coupled to said head, said cover having an open top end and an open bottom end wherein said cover is selectively positionable over said bristles when said head is positioned between said open top and bottom ends and is selectively positionable on said neck below said bristles when said cover is pushed downward away from said bristles;
- a coupler removing couples said neck and said handle;
- a toothpaste cartridge positionable in said interior space of said handle, said toothpaste cartridge being cylindrical and configured to store and dispense toothpaste, a bottom side of said toothpaste cartridge having a thin covering, a top side of said toothpaste cartridge having an outwardly projecting ring, said ring having an aperture positioned centrally therein;
- a conduit positioned in said elongated member, said conduit having a first end in fluid communication with said toothpaste cartridge and a second end positioned proximate said bristles wherein said conduit is configured for delivering toothpaste from said toothpaste cartridge to said bristles, said first end of said conduit being coupled to said ring of said toothpaste cartridge and said second end of said conduit being coupled to said hole in said head, said second end of said conduit comprising a curved portion wherein said curved portion is positioned parallel to said bristles when said surface is coupled to said head;
- an opening extending through said handle into said interior space wherein said opening is configured for selectively inserting and removing said toothpaste cartridge from said interior space, said opening extending through said top side of said handle;
- a door coupled to said handle, said door being selectively positionable such that said door closes said opening, said door being transparent wherein said door is configured for viewing a level of toothpaste held in said interior space;
- a motor coupled to said handle and extending across said interior space, said motor being positioned in a medial section of said handle;
- a battery compartment coupled to said handle, said battery compartment being positioned in said interior space in a bottom side of said handle, said battery compartment being configured for holding a pair of batteries, said battery compartment being electrically coupled to said motor wherein said battery compartment activates said motor and thereby moves said head when the batteries deliver power to said motor;
- an end cap couplable to said handle, said end cap being selectively couplable to said bottom side of said handle wherein said end cap is configured to store the batteries inside said battery compartment;
- a control coupled to said handle, said control being positioned on said top side of said handle below said opening, said control being operationally coupled to said motor and said battery compartment wherein selectively manipulating said control activates said motor, said control further comprising an off position and a plurality of speed settings, said speed settings comprising a low speed setting, a medium speed setting, and a high speed setting wherein said low speed setting is slower than said medium speed setting and said medium speed setting is slower than said high speed setting;
- a plunger coupled to said handle and extending across said interior space, said plunger coupling said toothpaste cartridge and said motor, said plunger being operationally engaged to said toothpaste cartridge;
- a button coupled to said handle, said button being operationally coupled to said plunger wherein said plunger engages said toothpaste cartridge upon manipulation of said button wherein said button is configured for dispensing toothpaste from said toothpaste cartridge to said bristles;

a coil coupled to said handle and extending across said interior space, said coil being positioned between said battery compartment and said motor, said coil being electrically coupled to said battery compartment and said motor;

a hub, said hub being substantially oval-shaped;

a cup couplable to said hub, said cup having a bottom end and a peripheral wall extending upwardly from said bottom end wherein said bottom end and said peripheral wall define an interior space for holding a fluid;

a toothbrush cavity coupled to said hub, said toothbrush cavity extending downwardly into a top side of said hub, said toothbrush cavity having a size and shape corresponding to said bottom side of said handle wherein said toothbrush cavity is configured to receive said elongated member when said bottom side of said handle is positioned in said toothbrush cavity;

a cup cavity coupled to said hub, said cup cavity extending downwardly into said top side of said hub, said cup cavity having a size and shape corresponding to said bottom end of said cup wherein said cup cavity is configured to receive said cup when said bottom end of said cup is positioned in said cup cavity;

a power cord being coupled to said hub, said power cord extending outwardly from one of a plurality of sides of said hub, a first end of said power cord being retractable into said hub, said power cord being operationally coupled to said hub wherein said power cord is configured to deliver power to said hub when said first end of said power cord is coupled to an electrical outlet;

a contact coupled to said end cap, said contact extending across an inner surface of said end cap, said contact forming a closed circuit when said handle is positioned in said toothbrush cavity and is receiving electrical power from said hub;

a suction cup coupled to said hub, said suction cup extending downwardly from a bottom side of said hub wherein said suction cup is configured to secure said suction cup to an exterior surface when said suction cup is pressed downwardly against the exterior surface;

a first indicator coupled to said handle, said first indicator being positioned below said opening and above said control, said first indicator being operationally coupled to said battery compartment wherein said first indicator emits a charged light when the batteries in said battery compartment have a full charge and emits an uncharged light when the batteries are low on charge; and a second indicator coupled to said hub, said second indicator being positioned on one of said sides of said hub, said second indicator being operationally coupled to said battery compartment wherein said second indicator emits a charged light when the batteries in said battery compartment have a full charge and emits an uncharged light when the batteries are low on charge.

\* \* \* \* \*